US006977315B2

(12) United States Patent
Yamada et al.

(10) Patent No.: US 6,977,315 B2
(45) Date of Patent: Dec. 20, 2005

(54) PROCESS FOR PRODUCING OPTICALLY ACTIVE NITROALCOHOLS

(75) Inventors: Tohru Yamada, Yokohama (JP); Taketo Ikeno, Yokohama (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/979,795

(22) Filed: Nov. 2, 2004

(65) Prior Publication Data

US 2005/0215832 A1   Sep. 29, 2005

(30) Foreign Application Priority Data

Mar. 24, 2004  (JP) .............................. 2004-086888

(51) Int. Cl.$^7$ .......................................... C07L 205/00
(52) U.S. Cl. ...................... 568/705; 568/583; 568/587; 568/704; 568/709
(58) Field of Search .............................. 568/705, 709, 568/704, 583, 587

(56) References Cited

U.S. PATENT DOCUMENTS

| 5,756,790 A | 5/1998 | Mukaiyama et al. |
| 6,610,889 B2 | 8/2003 | Trost et al. |

FOREIGN PATENT DOCUMENTS

| JP | 6-154618 | 6/1994 |
| JP | 9-151143 | 6/1997 |
| JP | 9-253502 | 9/1997 |
| JP | 9-255631 | 9/1997 |

OTHER PUBLICATIONS

Sasai et al., "Basic Character of Rare Earth Metal Alkoxides Utilization in Catalytic C-C Bond-Forming Reactions and Catalytic Asymmetric Nitroaldol Reactions", *J. Am. Chem. Soc.*, 114, pp. 4418-4420 (1992); American Chemical Society.

Sasai et al., "Catalytic Asymmetric Nitroaldol Reaction: An Efficient Synthesis of (S) Propranolol Using the Lanthanum Binaphthol Complex", *Tetrahedron Letters*, 34, No. 5, pp. 855-858 (1993), Pergamon Press Ltd., Great Britain.

Sasai et al., "Efficient Diastereoselective and Enantioselective Nitroaldol Reactions from Prochiral Starting Materials: Utilization of La-Li-6,6'-Disubstituted BINOL Complexes as Asymmetric Catalysts", *J. Org. Chem.* 60, pp. 7388-7389 (1995), American Chemical Society.

Trost et al., "A Dinuclear Zn Catalyst for the Asymmetric Nitroaldol (Henry) Reaction", *Angew. Chem. Int. Ed.* 2002, 41, No. 5, pp. 861-863 (2002), Wiley-VCH Verlag GmbH, Germany.

Nishida et al. "Effects of Substituents in the Chelate Ring on the Electronic State of Tetraazamacrocyclic Complexes of Cobalt(II), Nickel(II) and Copper(II)", *Inorganica Chimic Acta*, 38, pp. 213-219 (1980), Elsevier Sequoia S.A., Lausanne, Switzerland.

*Ann. Chem.* 297, pp. 57-74 (1897)* no translation.
*Z. Chem.* 8 pp. 30-31 (1968)* no translation.
*Z. Chem.* 8 pp. 392-393 (1968)* no translation.

*Primary Examiner*—Michael L. Shippen
(74) *Attorney, Agent, or Firm*—Buchanan Ingersoll PC

(57) ABSTRACT

The present invention relates to a process for producing optically active β-nitroalcohols wherein nitroaldol reactions of aldehydes and nitroalkanes are carried out in the presence of a base and an optically active metal complex catalyst represented by the following formula (c):

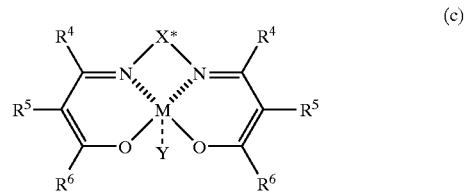

(where $R^4$, $R^5$, and $R^6$ represent a hydrogen atom, an alkyl group, an alkenyl group, an aryl group, an acyl group, an alkoxycarbonyl group, or an aryloxycarbonyl group, and $R^5$ and $R^6$ may be linked together to form a ring; X* represents a hydrocarbon group having an asymmetric carbon atom or axial asymmetry; M represents a cobalt ion or a chromium ion; and Y represents an anion capable of forming a salt when the valence of M is larger than that of a ligand).

16 Claims, No Drawings

PROCESS FOR PRODUCING OPTICALLY ACTIVE NITROALCOHOLS

TECHNICAL FIELD

The present invention relates to a process for producing optically active β-nitroalcohols by nitroaldol reactions of aldehydes using an asymmetric catalyst. The optically active β-nitroalcohols are important intermediates of optically active aminoalcohols which are useful as starting materials in synthesizing fine chemicals and physiologically active compounds such as medicines and agricultural chemicals.

BACKGROUND ART

As a process for producing optically active nitroalcohols by nitroaldol reactions using an asymmetric catalyst, for example, there has been reported that optically active nitroalcohols are obtained with satisfactory results in chemical yield and asymmetric yield by reactions of aldehydes and nitroalkanes using an asymmetric catalyst composed of optically active binaphthols, rare earth metal compounds, and alkali metal compounds (See Japanese Unexamined Patent Application Publication Nos. 6-154618, 9-253502, and 9-255631, J. Am. Chem. Soc. vol. 114, p. 4418 (1992), Tetrahedron Letters, vol. 34, p. 855 (1993), and J. Org. Chem., vol. 60, p. 7388 (1995)).

There has also been reported that optically active nitroalcohols can be obtained by reactions of aldehydes and nitroalkanes using an asymmetric catalyst consisting of optically active binuclear zinc complexes (See, U.S. Pat. No. 6,610,889, and Angew. Chem. Int. Ed., vol. 41, p. 861 (2002)).

However, these processes have problems in that the reactions are required to be carried out for a long period of reaction time, and also equipments for low temperature reactions and a large amount of expensive asymmetric ligands or rare earth metal compounds are required. The methods described in U.S. Pat. No. 6,610,889, and in Angew. Chem. Int. Ed., vol. 41, p. 861 (2002) also have a problem in that the addition of molecular sieves is required, however these methods are not sufficient for practical use.

DISCLOSURE OF THE INVENTION

It is an object of the present invention to provide a process for producing optically active nitroalcohols with high productivity from the viewpoint of reaction efficiency such as a reaction time or an amount of catalyst used.

In the present invention, nitroalcohols are produced by reactions of aldehydes and nitroalkanes in the presence of a base and a specific metal complex having an optically active Schiff base as a ligand. That is, the present invention includes the following construction.

(1) A process for producing optically active β-nitroalcohols, wherein nitroaldol reactions of aldehydes and nitroalkanes are carried out in the presence of a base and an optically active metal complex catalyst represented by the following formula (c):

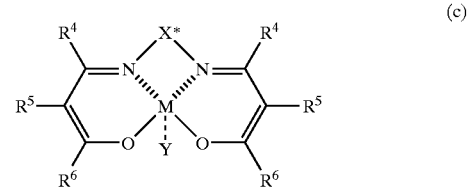

(where $R^4$, $R^5$, and $R^6$ represent independently a hydrogen atom, a straight, branched or cyclic alkyl group, a straight or branched alkenyl group, an aryl group, an acyl group, an alkoxycarbonyl group, an aryloxycarbonyl group, or an aralkyloxycarbonyl group, each of which may have a substituent, and $R^5$ and $R^6$ may be linked together to form a ring; X* represents a hydrocarbon group of 4 or more carbon atoms having an asymmetric carbon atom or axial asymmetry; M represents a cobalt ion or a chromium ion; and Y represents an anion capable of forming a salt when the valence of M is larger than that of a ligand, and Y does not exist when the valences of a metal ion and a ligand are equal to each other).

(2) The process for producing optically active β-nitroalcohols according to (1), wherein the aldehydes are represented by the following general formula (a):

$$R^1CHO \qquad (a)$$

(where $R^1$ represents a straight, branched or cyclic alkyl group, a straight, branched or cyclic alkenyl group, a straight or branched alkynyl group, an aryl group, an aralkyl group, an aralkenyl group, or an aralkynyl group, each of which may have a substituent).

(3) The process for producing optically active β-nitroalcohols according to (1), wherein the nitroalkanes are represented by the following general formula (b):

(where $R^2$ and $R^3$ represent independently a hydrogen atom or an optionally substituted alkyl group, and $R^2$ and $R^3$ may be linked together to form a ring).

(4) The process for producing optically active β-nitroalcohols according to (2), wherein the nitroalkanes are represented by the general formula (b).

(5) The process for producing optically active β-nitroalcohols according to (1), wherein the hydrocarbon group X* in the general formula (c) is a hydrocarbon group represented by any one of the following general formulas (x-1), (x-2), and (x-3):

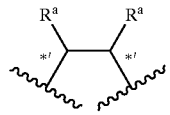

-continued

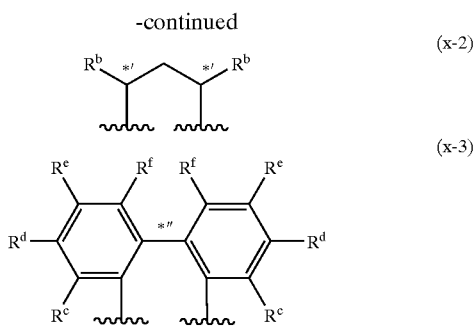

(where $R^a$ and $R^b$ represent a straight, branched or cyclic alkyl group, or an aryl group, each of which may have a substituent, and two $R^a$ groups may be linked together to form a ring; $R^c$, $R^d$, $R^e$, and $R^f$ represent independently a hydrogen atom, a halogen atom, a straight, branched or cyclic alkyl group, an aryl group, or an alkoxy group, each of which may have a substituent, $R^e$ and $R^f$ may be linked together to form a ring, and the ring may have a substituent; *' represents an asymmetric carbon atom; and *" represents axial asymmetry).

(6) The process for producing optically active β-nitroalcohols according to (2), wherein the hydrocarbon group X* in the general formula (c) is a hydrocarbon group represented by any one of the general formulas (x-1), (x-2), and (x-3).

(7) The process for producing optically active β-nitroalcohols according to (3), wherein the hydrocarbon group X* in the general formula (c) is a hydrocarbon group represented by any one of the general formulas (x-1), (x-2), and (x-3).

(8) The process for producing optically active β-nitroalcohols according to (4), wherein the hydrocarbon group X* in the general formula (c) is a hydrocarbon group represented by any one of the general formulas (x-1), (x-2), and (x-3).

(9) The process for producing optically active β-nitroalcohols according to any one of (1) to (8), wherein the base is a compound selected from the group consisting of primary amines, secondary amines, and tertiary amines.

BEST MODE FOR CARRYING OUT THE INVENTION

Hereinafter, the process for producing optically active nitroalcohols according to the present invention will be described in detail.

[Aldehydes]

Aldehydes used as a starting material can be suitably selected corresponding to the optically active nitroalcohols which are desired in the present invention.

As the aldehydes used as the starting material, preferred is a compound represented by the following general formula (a):

$$R^1CHO \qquad (a)$$

In the general formula (a), $R^1$ includes a straight, branched or cyclic alkyl group, a straight, branched or cyclic alkenyl group, a straight or branched alkynyl group, an aryl group, an aralkyl group, an aralkenyl group, and an aralkynyl group, each of which may have a substituent.

As the straight or branched alkyl group in $R^1$, preferred is a substituted or unsubstituted alkyl group having 1 to 20 carbon atoms, and the substituent includes a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, and a silyl group having 18 or less carbon atoms. Examples of the straight or branched alkyl group in $R^1$ include a methyl group, an ethyl group, an n-propyl group, an isopropyl group, an n-butyl group, a sec-butyl group, a tert-butyl group, an n-pentyl group, a 2-pentyl group, a 3-pentyl group, an isopentyl group, a neopentyl group, a tert-pentyl group, an n-hexyl group, a 2-hexyl group, a 3-hexyl group, an n-octyl group, an n-nonyl group, an n-decyl group, an n-dodecyl group, a 1,1,2-trimethyl-n-propyl group, a 1,2,2-trimethyl-n-propyl group, and a 3,3-dimethyl-n-butyl group.

As the cyclic alkyl group in $R^1$, preferred is a substituted or unsubstituted cycloalkyl group having 3 to 10 carbon atoms, and the substituent includes a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, and a silyl group having 18 or less carbon atoms. Examples of the cyclic alkyl group in $R^1$ include a cyclopropyl group, a cyclobutyl group, a cyclopentyl group, and a cyclohexyl group.

As the straight or branched alkenyl group in $R^1$, preferred is a substituted or unsubstituted alkenyl group having 2 to 20 carbon atoms, and the substituent includes a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, and a silyl group having 18 or less carbon atoms. Examples of the straight or branched alkenyl group in $R^1$ include a vinyl group, an allyl group, an isopropenyl group, and a crotyl group.

As the cyclic alkenyl group in $R^1$, preferred is a substituted or unsubstituted cycloalkenyl group having 5 to 10 carbon atoms, and the substituent includes a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, and a silyl group having 18 or less carbon atoms. Examples of the cyclic alkenyl group in $R^1$ include a 1-cyclopentenyl group, a 1-cyclohexenyl group, and a 3-methyl-1-cyclohexenyl group.

As the straight or branched alkynyl group in the $R^1$, preferred is a substituted or unsubstituted alkynyl group having 2 to 20 carbon atoms, and the substituent includes a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, and a silyl group having 18 or less carbon atoms. Examples of the straight or branched alkynyl group in the $R^1$ include an ethynyl group, a 1-propynyl group, a 2-propynyl group, a 1-butynyl group, a 1-pentynyl group, a 1-heptynyl group, and a 2-trimethylsilyl-1-ethynyl group.

The aryl group in R¹ includes an aromatic hydrocarbon ring group such as a phenyl group and a naphthyl group, and an aromatic heterocyclic group containing a hetero atom such as O, S and N. These groups may have a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, a nitro group, a silyl group having 18 or less carbon atoms, as a substituent. As the aromatic hydrocarbon ring group, preferred is a substituted or unsubstituted phenyl group or naphthyl group. Examples of the aromatic hydrocarbon ring group include a phenyl group, an o-fluorophenyl group, an o-chlorophenyl group, an o-bromophenyl group, an o-trifluoromethylphenyl group, an o-tolyl group, an o-methoxyphenyl group, a p-fluorophenyl group, a p-chlorophenyl group, a p-bromophenyl group, a p-trifluoromethylphenyl group, a p-tolyl group, a p-methoxyphenyl group, a p-nitrophenyl group, a 2,3-dichlorophenyl group, a 2,4-dichlorophenyl group, a 2,6-dichlorophenyl group, a 2,3,5-trichlorophenyl group, a pentafluorophenyl group, an α-naphthyl group, and a β-naphthyl group. As the aromatic heterocyclic group, preferred is a monocyclic ring, a polycyclic ring, or a condensed ring having 4 to 10 carbon atoms. Examples of the aromatic heterocyclic group include a furan group, a thiophene group, a pyridine group, and an indenyl group.

As the aralkyl group in R¹, preferred is an aralkyl group of 7 to 20 carbon atoms having an aryl group such as phenyl, naphthyl and anthryl. The aryl group may have a substituent such as a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, a nitro group, or a silyl group having 18 or less carbon atoms. Examples of the aralkyl group include a benzyl group, an α-methylbenzyl group, a 2-phenetyl group, and a 3-phenylpropyl group.

As the aralkenyl group in R¹, preferred is an aralkenyl group of 8 to 20 carbon atoms having an aryl group such as phenyl, naphthyl and anthryl. The aryl group may have a substituent such as a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, a nitro group, or a silyl group having 18 or less carbon atoms. Examples of the aralkenyl group include a 2-phenylethenyl group.

As the aralkynyl group in R¹, preferred is an aralkynyl group of 8 to 20 carbon atoms having an aryl group such as phenyl, naphthyl and anthryl. The aryl group may have a substituent such as a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, a nitro group, or a silyl group having 18 or less carbon atoms. Examples of the aralkynyl group include a 2-phenylethynyl group.

Examples of the aldehydes represented by the general formula (a) include acetaldehyde, propionaldehyde, isopropylaldehyde, n-butylaldehyde, cyclopropylaldehyde, cyclohexylaldehyde, propenylacetaldehyde, crotonaldehyde, benzaldehyde, 2-fluorobenzaldehyde, 2-chlorobenzaldehyde, 2-bromobenzaldehyde, 2-trifluoromethylbenzaldehyde, 4-chlorobenzaldehyde, 3-phenylpropionaldehyde, 1-naphthaldehyde, 2-naphthaldehyde, cinnamaldehyde, and benzyloxyacetaldehyde.

[Nitroalkanes]

The nitroalkanes used in the production method according to the present invention are preferably those represented by the following general formula (b):

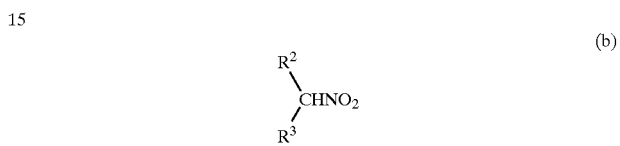

In the general formula (b), $R^2$ and $R^3$ are a hydrogen atom or an optionally substituted alkyl group, each of which may be linked together to form a ring.

As the alkyl groups in $R^2$ and $R^3$, preferred are straight or branched and substituted or unsubstituted alkyl groups having 1 to 20 carbon atoms, and the substituent includes a halogen atom such as fluorine, chlorine, bromine and iodine, a hydroxyl group, an alkoxy group having 12 or less carbon atoms, an alkoxycarbonyl group having 12 or less carbon atoms, an acyloxy group having 12 or less carbon atoms, an amino group having 12 or less carbon atoms, and a silyl group having 18 or less carbon atoms. Examples of the alkyl group in the $R^2$ and $R^3$ include a methyl group, an ethyl group, a n-propyl group, an isopropyl group, a n-butyl group, a n-pentyl group, a n-hexyl group, a n-heptyl group, an n-octyl group, a n-nonyl group, a n-decyl group, and a n-dodecyl group.

When $R^2$ and $R^3$ are linked together to form a ring, preferred is a saturated hydrocarbon ring or a saturated heterocyclic ring, and particularly preferred is a saturated hydrocarbon ring. The ring is preferably a 10 or less-membered ring formed together with carbon atoms to which $R^2$ and $R^3$ each are linked, and particularly preferably a 3- to 7-membered ring. For example, when $R^2$ and $R^3$ are linked together to form —(CH$_2$)$_2$— or —(CH$_2$)$_4$—, a cyclopropane ring or cyclopentane ring is formed. The ring may have a substituent, and for example, may be substituted by one substituent or two or more substituents selected from alkyl groups (preferably having 8 or less carbon atoms) such as a methyl group, an ethyl group, an n-propyl group, an isopropyl group, an n-butyl group, a sec-butyl group and a tert-butyl group, and aryl groups such as a phenyl group and a naphthyl group.

Examples of the nitroalkanes represented by the general formula (b) include nitromethane, nitroethane, 1-nitropropane, 2-nitropropane, 1-nitrobutane, 2-nitroethanol, and 2-benzyloxy-1-nitroethane.

[Optically Active Metal Complex]

In the method according to the present invention, when an optically active metal complex represented by the following general formula (c):

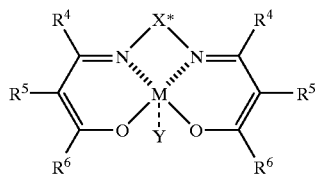

(c)

is used as a catalyst, it is preferable because optically active nitroalcohols are efficiently obtainable in high optical yield.

In the general formula (c), $R^4$, $R^5$, and $R^6$ may be the same or different from each other, and are a hydrogen atom, a straight, branched or cyclic alkyl group, a straight or branched alkenyl group, an aryl group, an acyl group, an alkoxycarbonyl group, an aryloxycarbonyl group, or an aralkyloxycarbonyl group, each of which may have a substituent. In addition, $R^5$ and $R^6$ may be linked together to form a ring.

As the alkyl groups in $R^4$, $R^5$, and $R^6$, preferred are straight, branched or cyclic alkyl groups having 1 to 10 carbon atoms, each of which may have a substituent. The substituent includes a halogen atom such as fluorine and chlorine, an alkoxy group having 12 or less carbon atoms, and a silyl group having 18 or less carbon atoms. Examples of the alkyl groups in $R^4$, $R^5$, and $R^6$ include a methyl group, an ethyl group, an n-propyl group, an isopropyl group, a sec-butyl group, a tert-butyl group, a cyclopentyl group, and a cyclohexyl group.

As the alkenyl groups in $R^4$, $R^5$, and $R^6$, preferred are straight or branched alkenyl groups having 2 to 10 carbon atoms, each of which may have a substituent. The substituent includes a halogen atom such as fluorine and chlorine, an alkoxy group having 12 or less carbon atoms, and a silyl group having 18 or less carbon atoms. Examples of the alkenyl groups in $R^4$, the $R^5$, and the $R^6$ include a vinyl group and a 2-propenyl group.

As the aryl groups in $R^4$, $R^5$, and $R^6$, preferred are a phenyl group and a naphthyl group, each of which may have a substituent such as a halogen atom such as fluorine and chlorine, a nitro group, an alkyl group having 12 or less carbon atoms, and an alkoxy group having 12 or less carbon atoms. As the alkyl group and the alkoxy group in the substituents, preferred are those having 4 or less carbon atoms. Examples of the aryl group in $R^4$, $R^5$, and $R^6$ include substituted or unsubstituted aromatic hydrocarbon groups such as a phenyl group, a p-methoxyphenyl group, a p-chlorophenyl group, p-fluorophenyl group, 3,5-dimethylphenyl group, 2,4,6-trimethylphenyl group, 2,6-diisopropylphenyl group, an α-naphthyl group, and a β-naphthyl group.

Examples of the acyl groups in $R^4$, $R^5$, and $R^6$ include an aliphatic acyl group and an aromatic acyl group.

As the aliphatic acyl group, for example, preferred is an acyl group having 2 to 10 carbon atoms such as an acetyl group, a trifluoroacetyl group, a propionyl group, a butyryl group, an isobutyryl group and a pivaloyl group. These may be substituted by a halogen atom such as fluorine or an alkoxy group having 12 or less carbon atoms.

As the aromatic acyl group, preferred is an arylcarbonyl group which may have a substituent such as a halogen atom, a nitro group, an alkyl group having 12 or less carbon atoms, or an alkoxy group having 12 or less carbon atoms, on an aryl group such as phenyl, naphthyl and anthryl. The alkyl group and the alkoxy group in the substituents are preferably those having 4 or less carbon atoms. Examples of the groups include a benzoyl group, 3,5-dimethylbenzoyl group, a 2,4,6-trimethylbenzoyl group, a 2,6-dimethoxybenzoyl group, a 2,4,6-trimethoxybenzoyl group, a 2,6-diisopropoxybenzoyl group, an α-naphthylcarbonyl group, a β-naphthylcarbonyl group, and a 9-anthrylcarbonyl group.

As the alkoxycarbonyl groups in $R^4$, $R^5$, and $R^6$, preferred are straight, branched or cyclic alkoxycarbonyl groups having 2 to 20 carbon atoms, each of which may have a substituent. The substituent includes a halogen atom such as fluorine and an alkoxy group having 12 or less carbon atoms. Examples of the alkoxycarbony group include a methoxycarbonyl group, an ethoxycarbonyl group, an n-butoxycarbonyl group, an n-octyloxycarbonyl group, a cyclopentyloxycarbonyl group, a cyclohexyloxycarbonyl group, a cyclooctyloxycarbonyl group, and a tert-butoxycarbonyl group.

As the aryloxycarbonyl groups in $R^4$, $R^5$, and $R^6$, preferred are aryloxycarbonyl groups of 7 to 20 carbon atoms having an aryl group such as phenyl, naphthyl and anthryl. These groups may have a substituent such as a halogen atom, a nitro group, an alkyl group having 12 or less carbon atoms, or an alkoxy group having 12 or less carbon atoms, on the aryl group. The alkyl group and the alkoxy group in the substituents are preferably those having 4 or less carbon atoms. Examples of the aryloxycarbonyl group include a phenoxycarbonyl group, a 2,6-dimethylphenoxycarbonyl group, an α-naphthyloxycarbonyl group, and a β-naphthyloxycarbonyl group.

As the aralkyloxycarbonyl groups in $R^4$, $R^5$, and $R^6$, preferred are aralkyloxycarbonyl groups of 8 to 20 carbon atoms having an aryl group such as phenyl, naphthyl and anthryl. These groups may have a substituent such as a halogen atom, a nitro group, an alkyl group having 12 or less carbon atoms, or an alkoxy group having 12 or less carbon atoms, on the aryl group. The alkyl group and the alkoxy group in the substituents are preferably those having 4 or less carbon atoms. Examples of the aralkyloxycarbonyl group include a benzyloxycarbonyl group and a phenetyloxycarbonyl group.

In addition, $R^5$ and $R^6$ may be linked together to form a ring together with carbon atoms to which $R^5$ and $R^6$ each are linked. The ring is preferably an aliphatic or aromatic hydrocarbon ring. The formed ring may be a condensed ring. The aliphatic hydrocarbon ring is preferably a 10 or less-membered ring, particularly preferably a 3- to 7-membered ring, and most preferably a 6-membered ring. The aromatic hydrocarbon ring is preferably 6-membered ring, that is, a benzene ring. For example, when $R^5$ and $R^6$ are linked together to form —(CH$_2$)$_4$— or —CH=CH—CH=CH—, a cyclohexene ring or a benzene ring is formed, respectively.

The ring formed as described above may be substituted by one substituent or two or more substituents selected from alkyl groups such as a methyl group, an ethyl group, an n-propyl group, an isopropyl group, an n-butyl group, a sec-butyl group and a tert-butyl group; aryl groups such as a phenyl group and a naphthyl group; aralkyl groups such as a benzyl group and a 1-methyl-1-phenetyl group; alkoxy groups such as a methoxy group, an ethoxy group and an isopropoxy group; aryloxy groups such as a phenoxy group and a 2,6-dimethylphenoxy group; aralkyloxy groups such as a benzyloxy group, a 1-phenetyloxy group and a 2-phenetyloxy group; halogen atoms such as fluorine, chlorine and bromine; cyano group; nitro group; and silyl groups such as a trimethylsilyl group. In addition, the benzene rings may be condensed to form a polycyclic condensed ring such as a naphthalene ring. As the alkyl groups in the substituents, preferred are those having 8 or less carbon atoms.

M represents a cobalt ion or a chromium ion, and preferably a divalent or trivalent cobalt ion or a trivalent chromium ion.

Y represents an anion capable of forming a salt. When the valence of M is larger than that of a ligand, an electric charge is neutralized by Y. When the valence of a metal ion is the same as that of a ligand, Y does not exist. Examples of Y include $F^-$, $Cl^-$, $Br^-$, $I^-$, $OH^-$, $CH_3CO_2^-$, $p\text{-}CH_3C_6H_4SO_3^-$, $CF_3SO_3^-$, $PF_6^-$, $BF_4^-$, $BPh_4^-$, $SbF_6^-$, $ClO_4^-$, etc.

In the above-mentioned general formula (c), $X^*$ is a hydrocarbon group of 4 or more carbon atoms having an asymmetric carbon atom or axial asymmetry, and preferably an optically active divalent hydrocarbon group having 30 or less carbon atoms. The hydrocarbon group may have a substituent.

As the hydrocarbon group in the above-mentioned $X^*$, optically active hydrocarbon groups represented by the following general formulas (x-1) to (x-3) are suitable.

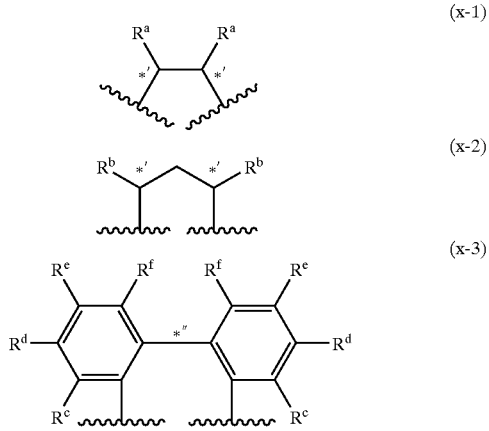

In the general formula (x-1), $R^a$ is a straight, branched or cyclic alkyl group, or an aryl group, each of which may have a substituent. Two $R^a$ groups may be linked together to form a ring. *' represents an asymmetric carbon atom.

As the straight, branched or cyclic alkyl group in $R^a$, preferred is a substituted or unsubstituted alkyl group having 1 to 10 carbon atoms. The substituent includes a halogen atom such as fluorine and an alkoxy group having 12 or less carbon atoms. Examples of the alkyl group in $R^a$ include a methyl group, an ethyl group, an n-propyl group, an isopropyl group, an n-butyl group, a sec-butyl group, a tert-butyl group, a cyclopentyl group, and a cyclohexyl group.

As the aryl group in $R^a$, preferred are a phenyl group and a naphthy group. These groups may have a substituent such as a halogen atom such as fluorine, chlorine, bromine and iodine, a nitro group, an alkyl group having 12 or less carbon atoms, or an alkoxy group having 12 or less carbon atoms. As the alkyl group and the alkoxy group in the substituents, preferred are those having 4 or less carbon atoms. Examples of the aryl group in $R^a$ include substituted or unsubstituted aromatic hydrocarbon groups such as a phenyl group, a p-fluorophenyl group, a p-trifluoromethylphenyl group, a p-tolyl group, a p-methoxyphenyl group, a 3,5-dimethylphenyl group, a 3,5-dimethoxyphenyl group, a 3,5-diisopropoxyphenyl group, a 2,4,6-trimethylphenyl group, a 2,4,6-trimethoxyphenyl group, a 2,4,6-triisopropoxyphenyl group, a pentafluorophenyl group, an α-naphthyl group, and a β-naphthyl group.

In addition, when two $R^a$ groups are linked together to form a ring, examples of the rings include a saturated hydrocarbon ring, an aliphatic or aromatic hydrocarbon ring having unsaturated bonds, and a saturated heterocyclic ring. The saturated hydrocarbon ring is preferable. As the ring, preferred is a 10 or less-membered ring formed together with carbon atoms to which two $R^a$ groups are linked, more preferred is a 5- to 7-membered ring, and most preferred is a 6-membered ring. When two $R^a$ groups are linked together to form $—(CH_2)_4—$ group, a 6-membered ring is formed.

As $R^a$, an aryl group is particularly preferred in that optically active nitroalcohols can be obtained in high optical yield.

In the general formula (x-2), $R^b$ is a straight, branched or cyclic alkyl group, or an aryl group, each of which may have a substituent. *' represents an asymmetric carbon atom.

As the straight, branched or cyclic alkyl group in $R^b$, preferred is a substituted or unsubstituted alkyl group having 1 to 10 carbon atoms. The substituent includes a halogen atom such as fluorine and an alkoxy group having 12 or less carbon atoms. Examples of the alkyl group in $R^b$ include a methyl group, an ethyl group, a n-propyl group, an isopropyl group, a n-butyl group, a sec-butyl group, a tert-butyl group, a cyclopentyl group, and a cyclohexyl group.

As the aryl group in $R^b$, preferred are aromatic hydrocarbon groups such as a phenyl group and a naphthy group. These groups may have a substituent such as a halogen atom such as fluorine, chlorine, bromine and iodine, a nitro group, an alkyl group having 12 or less carbon atoms, or an alkoxy group having 12 or less carbon atoms. As the alkyl group and the alkoxy group in the substituents, preferred are those having 4 or less carbon atoms. Examples of the aryl group in $R^b$ include a phenyl group, a p-fluorophenyl group, a p-trifluoromethylphenyl group, a p-tolyl group, p-methoxyphenyl group, a 3,5-dimethylphenyl group, a 3,5-dimethoxyphenyl group, a 3,5-diisopropoxyphenyl group, a 2,4,6-trimethylphenyl group, a 2,4,6-trimethoxyphenyl group, a 2,4,6-triisopropoxyphenyl group, a pentafluorophenyl group, an α-naphthyl group, and a β-naphthyl group.

In the general formula (x-3), $R^c$, $R^d$, $R^e$, and $R^f$ may be the same or different from each other, and are independently a hydrogen atom, a halogen atom, a straight, branched or cyclic alkyl group, an aryl group, or an alkoxy group, each of which may have a substituent. In addition, $R^e$ and $R^f$ may be linked together to form a ring, and the ring may have a substituent. *" represents axial asymmetry.

Examples of the halogen atom in $R^c$, $R^d$, $R^e$, and $R^f$ include fluorine, chlorine, bromine, and iodine.

As the alkyl groups in $R^c$, $R^d$, $R^e$, and $R^f$, preferred are straight, branched or cyclic alkyl groups having 1 to 10 carbon atoms, each of which may have a substituent. The substituent includes a halogen atom such as fluorine, chlorine, bromine and iodine, an alkyl group having 12 or less carbon atoms, and an alkoxy group having 12 or less carbon atoms. Examples of the alkyl group in $R^c$, $R^d$, $R^e$, and $R^f$ include a methyl group, an ethyl group, a n-propyl group, an isopropyl group, a n-butyl group, a sec-butyl group, a tert-butyl group, a cyclopentyl group, and a cyclohexyl group.

As the aryl groups in $R^c$, $R^d$, $R^e$, and $R^f$, preferred are a phenyl group and a naphthy group. These groups may have a substituent such as a halogen atom such as fluorine, chlorine, bromine and iodine, a nitro group, an alkyl group having 12 or less carbon atoms, or an alkoxy group having 12 or less carbon atoms. As the alkyl group and the alkoxy group in the substituents, preferred are those having 4 or less carbon atoms. Examples of the aryl groups in $R^c$, $R^d$, $R^e$, and $R^f$ include a phenyl group, an α-naphthyl group, and a β-naphthyl group.

As the alkoxy groups in $R^c$, $R^d$, $R^e$, and $R^f$, preferred are alkoxy groups having 1 to 6 carbon atoms, each of which may have a substituent. The substituent includes a halogen atom such as fluorine. Examples of the alkoxy groups in $R^c$, $R^d$, $R^e$, and $R^f$ include a methoxy group, an ethoxy group, a n-propoxy group, an isopropoxy group, and a tert-butoxy group.

In addition, $R^e$ and $R^f$ may be linked together to form a ring together with carbon atoms to which $R^e$ and $R^f$ each are linked. The ring may be an aliphatic ring or an aromatic ring, and each ring may form a condensed ring and may form a heterocyclic ring containing an oxygen atom. The aliphatic ring (including an aliphatic heterocyclic ring) is preferably a 10 or less-membered ring, more preferably a 3- to 7-membered ring, and most preferably a 6-membered ring. The aromatic hydrocarbon ring is preferably a 6-membered ring, that is, a benzene ring. For example, when $R^e$ and $R^f$ are linked together to form —CH=CH—CH=CH—, —(CH$_2$)$_4$—, or OCH$_2$O—, formed is a benzene ring, a cyclohexane ring, or a dioxolane ring, respectively.

The ring formed as described above may be substituted by one substituent or two or more substituents selected from halogen atoms such as fluorine, chlorine and bromine; straight, branched or cyclic alkyl groups such as a methyl group, an ethyl group, a n-propyl group, an isopropyl group, a tert-butyl group, a cyclopentyl group, and a cyclohexyl group; straight or branched alkoxy groups such as a methoxy group, an ethoxy group, a n-propoxy group, an isopropoxy group, and a tert-butoxy group; aryl groups such as a phenyl group, an α-naphthyl group, and a β-naphthyl group. In addition, the benzene ring may be condensed to form a polycyclic condensed ring such as a naphthalene ring. The alkoxy groups in the substituents are preferably those having 8 or less carbon atoms.

Examples of the optically active cobalt (II) complex catalyst represented by the general formula (c) include those represented by the following formulas (c-1) to (c-10), and their enantiomers.

(c-1)
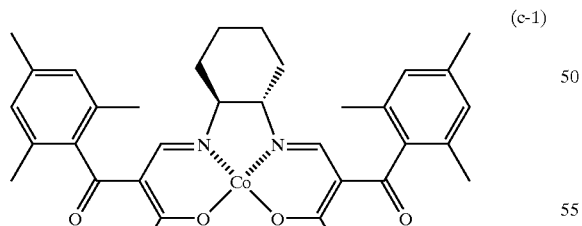

(c-2)
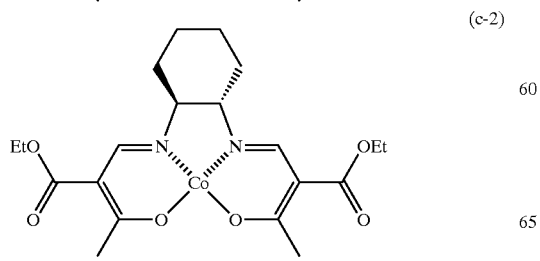

(c-3)
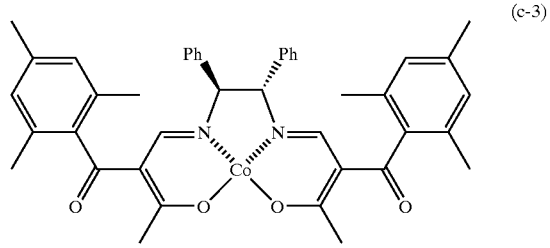

(c-4)
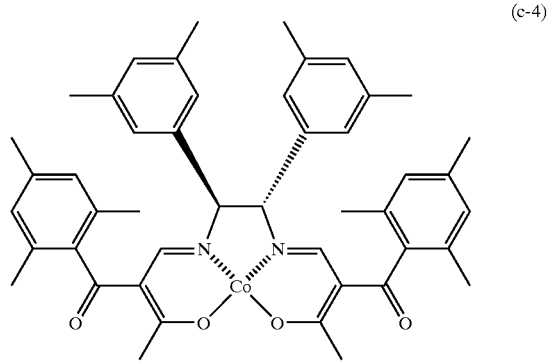

(c-5)
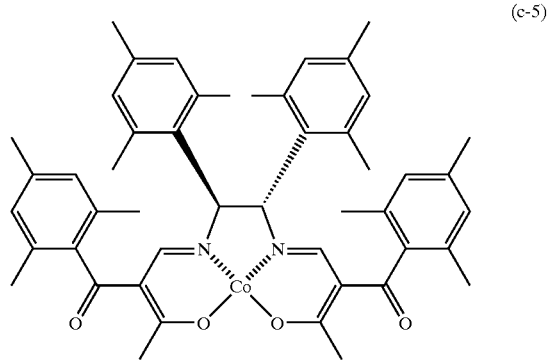

(c-6)
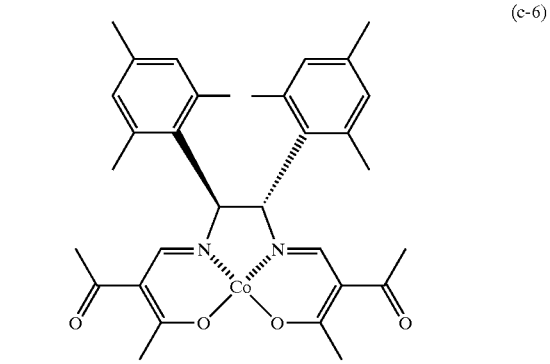

(c-7)
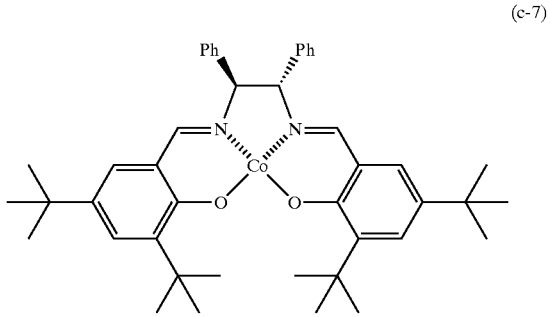

(c-8)
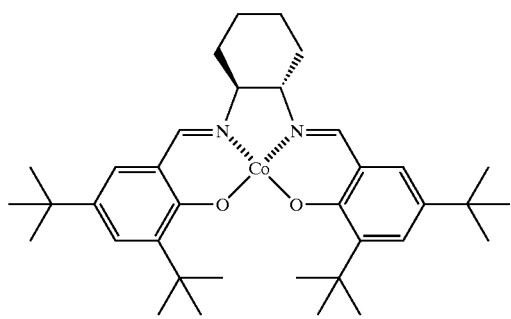

(c-9)
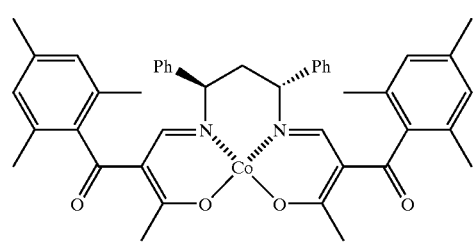

(c-10)
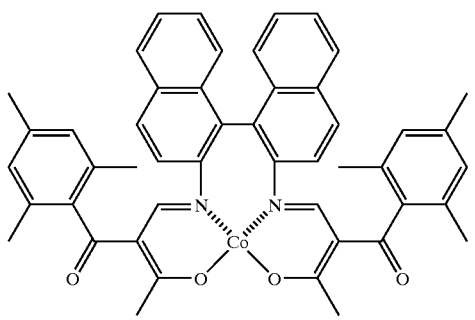

The optically active cobalt (III) complex catalyst represented by the general formula (c) includes optically active cobalt (III) complexes having the same ligand as those in the formulas (c-1) to (c-10). Examples of anions in the optically active cobalt (III) complexes include $F^-$, $Cl^-$, $Br^-$, $I^-$, $OH^-$, $CH_3CO_2^-$, p-$CH_3C_6H_4SO_3^-$, $CF_3SO_3^-$, $PF_6^-$, $BF_4^-$, $BPh_4^-$, $SbF_6^-$, $ClO_4^-$, etc. Examples of the optically active cobalt (III) complex catalyst include those represented by the following formulas (c-11) to (c-18), and their enantiomers.

(c-11)
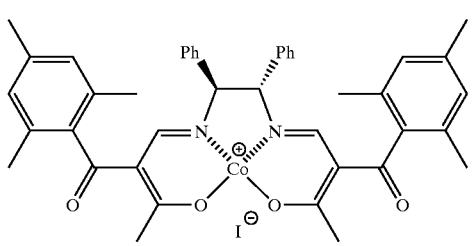

(c-12)
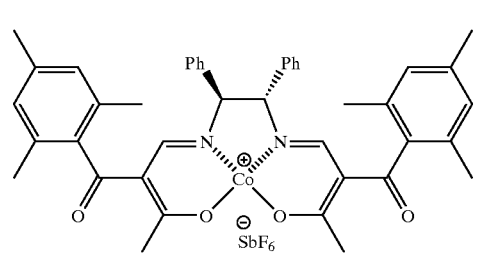

(c-13)
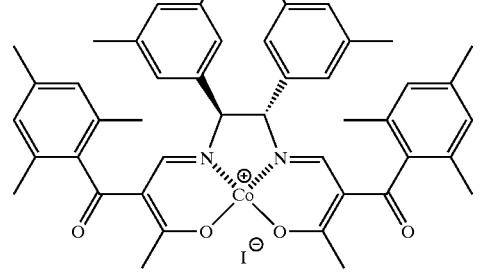

(c-14)
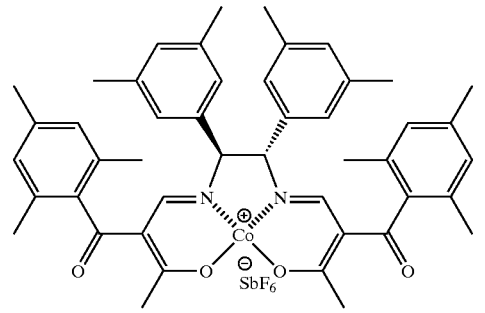

(c-15)

(c-16)

-continued (c-17)

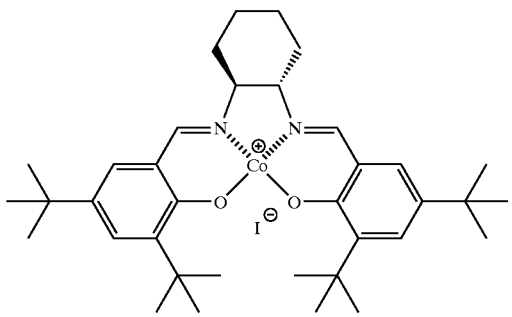

(c-18)

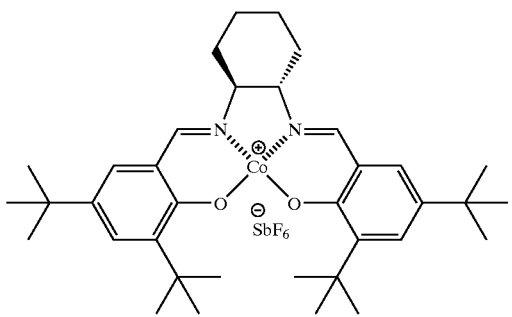

Example of the optically active chromium (III) complex catalyst represented by the general formula (c) includes an optically active chromium (III) complex having a chromium (III) ion instead of a cobalt (III) ion which is a central metal in the example of the optically active cobalt (III) complex catalyst.

Among these complexes, the optically active cobalt (II) complex and the optically active cobalt (III) complex are preferable in that optically active nitroalcohols are efficiently obtainable in high optical yield.

The optically active cobalt (II) complex and the optically active cobalt (III) complex represented by the formula (c) can be produced according to the known methods.

[Base]

In the present invention, it is preferable that a reaction is carried out in the coexistence of a base. That is, a base is added into the reaction system to accelerate the reaction and thus it is possible to effectively obtain the optically active nitroalcohols which are desired in the present invention. As the base to be added, preferred is a compound selected from the group consisting of primary amines, secondary amines, and tertiary amines from the viewpoint of yield and optical yield.

As the base, preferred is a compound represented by the following general formula (d):

(d)

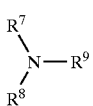

In the general formula (d), $R^7$, $R^8$, and $R^9$ are independently a hydrogen atom, or a straight, branched or cyclic alkyl group which may have a substituent. Further, at least two of $R^7$, $R^8$, and $R^9$ may be linked together to form a ring. The ring may further contain a hetero atom in addition to N to which $R^7$, $R^8$, and $R^9$ are linked.

It is preferable that $R^7$, $R^8$, and $R^9$ are not simultaneously hydrogen atoms.

As the alkyl groups in $R^7$, $R^8$, and $R^9$, preferred are substituted or unsubstituted alkyl groups having 1 to 10 carbon atoms. The substituent includes a halogen atom such as fluorine and chlorine, a hydroxyl group, an alkoxy group having 12 or less carbon atoms, and an amino group having 12 or less carbon atoms. Examples of the alkyl groups in $R^7$, $R^8$, and $R^9$ include a methyl group, an ethyl group, an n-propyl group, an isopropyl group, a n-butyl group, a sec-butyl group, a tert-butyl group, a n-pentyl group, a n-hexyl group, a cyclohexyl group, an n-octyl group, a n-nonyl group, and a n-decyl group.

In addition, at least two of $R^7$, $R^8$, and $R^9$ may be linked together to form a ring. The ring may further contain a hetero atom such as nitrogen or oxygen in addition to a nitrogen atom to which $R^7$, $R^8$, and $R^9$ are linked.

The ring is preferably a saturated ring (that is, a saturated heterocyclic ring containing one or more hetero atoms). When the ring further contains a nitrogen atom, the ring is formed as the form of —NR— (where R represents a hydrogen atom, or a straight or branched alkyl group having 8 or less carbon atoms). For example, when $R^7$ and $R^8$ are linked together to form —(CH$_2$)$_4$—, —(CH$_2$)$_5$—, —(CH$_2$)$_2$NMe(CH$_2$)$_2$—, or —(CH$_2$)$_2$O(CH$_2$)$_2$—, formed is a pyrrolidine ring, a piperidine ring, a piperazine ring, or a morpholine ring, respectively.

These rings may be substituted by an alkyl group such as a methyl group and an ethyl group or an alkoxy group. The alkyl group and the alkoxy group are preferably those having 8 or less carbon atoms. Examples of a group having a substituent in the formed ring include —CMe$_2$(CH$_2$)$_3$CMe$_2$—.

The base compound represented by the general formula (d) may have two or more nitrogen atoms.

Representative examples of the base represented by the general formula (d) include cyclohexylamine, tert-butylamine, tert-amylamine, diisopropylamine, diisobutylamine, di-secbutylamine, tert-butylisopropylamine, tertbutylcyclohexylamine, triethylamine, tert-butyldiethylamine, diisopropylethylamine, ethyldicyclohexylamine, 1-butylpyrrolidine, 1-ethylpiperidine, 4-ethylmorpholine, 1,3,5-triethylhexahydro-1,3,5-triazine, and 1,2,2,6,6-pentamethylpiperidine.

Among these bases, preferred are tertiary amines (where all of $R^7$, $R^8$, and $R^9$ are not a hydrogen atom) in that optically active nitroalcohols are efficiently obtainable in high optical yield in a short time. Examples of these bases include tert-butyldiethylamine, diisopropylethylamine, and 1,2,2,6,6-pentamethylpiperidine.

The base may be used alone or in combination of two or more.

[Asymmetric Nitroaldol Reaction]

Hereinafter, the process for carrying out asymmetric nitroaldol reactions according to the present invention will be described.

The reactions of aldehydes and nitroalkanes are carried out in no solvent or in the presence of a suitable solvent by using the optically active metal complex compound represented by the general formula (c) as a catalyst and by adding a base. As the base, the compound represented by the general formula (d) is suitable.

The amount of the nitroalkanes used is preferably 1 to 100 times moles, and more preferably 5 to 50 times moles, based on the aldehydes. The optically active metal complex compound represented by the general formula (c) is preferably used in an amount of 0.1 to 10 mol %, and more preferably 0.5 to 8 mol %, based on the aldehydes.

The amount of the base used is preferably 0.1 to 20 times moles, and more preferably 0.2 to 10 times moles, based on the aldehydes.

Examples of the reaction solvent include halogenated hydrocarbons such as dichloromethane, dichloroethane, and carbon tetrachloride; ethers such as tetrahydrofuran, diethyl ether, tert-butylmethyl ether, cyclopentylmethyl ether, and dimethoxyethane; alcohols such as methanol, ethanol, 1-propanol, 2-propanol, 1-butanol, 2-butanol, isobutanol, and cyclohexanol; aromatic hydrocarbons such as benzene, toluene, xylene, mesitylene, chlorobenzene, and o-dichlorobenzene; aliphatic hydrocarbons such as n-hexane, cyclohexane, n-octane, and n-decane; esters such as methyl acetate, ethyl acetate, and butyl acetate; ketones such as acetone, methyl ethyl ketone, and methyl isobutyl ketone; nitriles such as acetonitrile and butyronitrile; amides such as N,N-dimethylformamide, N,N-dimethylacetamide, and N-methylpyrrolidone; ureas such as 1,3-dimethylimidazolidinone and tetramethylurea. These can be used alone or in combination.

The reaction temperature is usually in the range of −100 to 30° C., and preferably −80 to 10° C.

After termination of the reaction, an organic solvent is distilled off, and optically active nitroalcohols which are the reaction product can then be isolated by the conventionally known method such as methods using distillation or adsorption, extraction, recrystallization, and silica gel chromatography.

In order to determine the optical purity of the optically active nitroalcohols obtained above, the nitroalcohols can be analyzed as it is, or can be converted into their derivatives and then analyzed, by optically active chromatography columns or optical rotation.

Hereinafter, the present invention will be described in detail with reference to the following Examples, however, the present invention is not limited to these Examples.

EXAMPLE 1

Synthesis of (1R)-1-(2-naphthyl)-2-nitroethanol

A solution of N,N'-bis[2-(2,4,6-trimethylbenzoyl)-3-oxobutylidene] -(1S,2S)-bis(3,5-dimethylphenyl)ethylene-1,2-diaminato cobalt (II) complexes (7.53 mg, 0.01 mmol, 2 mol %; formula (c-4)) in dichloromethane (2.0 ml) was added into a reaction vessel at room temperature under a nitrogen atmosphere, and was cooled to −70° C. Thereafter, to the reaction vessel were added a solution of 2-naphthaldehyde (78.1 mg, 0.5 mmol) in dichloromethane (1.0 ml), a mixture of nitromethane (1.0 ml, 18.5 mmol) and dichloromethane (1.0 ml), and diisopropylethylamine (64.7 mg, 0.5 mmol) in this order. The reaction mixture was stirred for 76 hours, and THF containing water was then added into the reaction mixture to stop the reaction. After a usual aftertreatment was performed, the resultant crude product was separated and purified by silica gel chromatography (hexane:ethyl acetate=4:1) to give 1-(2-naphthyl)-2-nitroethanol (89.7 mg, yield 83%). The optical purity of the product was analyzed by high performance liquid chromatography (optical activation column: Chiralpak AD-H manufactured by DAICEL CHEMICAL INDUSTRIES, LTD.; EtOH 10% in hexane, flow rate 1.0 ml/min, 254 nm; retention time (−)-isomer 25.1 min, (+)-isomer 30.2 min). As a result, the optical purity was 81% ee. The specific rotation $[\alpha]_D^{29}$ was −30.4° (c 0.90, $CH_2Cl_2$).

EXAMPLES 2 AND 3

The reaction was carried out in the same manner used in Example 1 except that the reaction temperature was in the range between −70° C. and temperatures shown in Table 1. The reaction time, and the yield and the optical purity of the resultant (1R)-1-(2-naphthyl)-2-nitroethanol were shown in Table 1.

TABLE 1

| Example | Reaction temperature/ ° C. | Reaction time/ h | Yield/ % | Optical purity/ % ee |
|---|---|---|---|---|
| 1 | −70 | 76 | 83 | 81 |
| 2 | −60 | 67 | quantitative | 69 |
| 3 | −40 | 36 | 93 | 61 |

EXAMPLES 4 TO 8

The reaction was carried out in the same manner used in Example 3 except that the amine compounds shown in Table 2 were used as a base instead of diisopropylethylamine. The reaction time, and the yield and the optical purity of the resultant (1R)-1-(2-naphthyl)-2-nitroethanol were shown in Table 2.

TABLE 2

| Example | Base | Reaction time/ h | Yield/ % | Optical purity/ % ee |
|---|---|---|---|---|
| 3 | Diisopropylethylamine | 36 | 93 | 61 |
| 4 | Diisopropylamine | 42 | 50 | 48 |
| 5 | Triethylamine | 27 | 64 | 54 |
| 6 | Dicyclohexylmethylamine | 20 | 72 | 45 |
| 7 | tert-Butyldiethylamine | 45 | quantitative | 55 |
| 8 | 1,2,2,6,6-Pentamethylpiperidine | 20 | 96 | 67 |

EXAMPLES 9 TO 13

Synthesis of (1R)-1-(2-chlorophenyl)-2-nitroethanol

The reaction was carried out in the same manner used in Example 2 except that 2-chlorobenzaldehyde was used instead of 2-naphthaldehyde, and the amount (times moles) of diisopropylethylamine used as a base, was the amounts shown in Table 3, based on aldehyde. The reaction time, and the yield and the optical purity of the resultant (1R)-1-(2-chlorophenyl)- 2-nitroethanol were shown in Table 3.

TABLE 3

| Example | Amount of i-$Pr_2$NEt (vs aldehydes) | Reaction time/ h | Yield/ % | Optical purity/ % ee |
|---|---|---|---|---|
| 9 | 0.25 | 96 | 95 | 77 |
| 10 | 0.5 | 98 | 98 | 80 |
| 11 | 1.0 | 18 | quantitative | 83 |
| 12 | 2.0 | 18 | quantitative | 84 |
| 13 | 5.0 | 3 | quantitative | 84 |

EXAMPLE 14

The reaction was carried out in the same manner used in Example 11 except that acetone was used as a solvent instead of dichloromethane and the reaction temperature was −70° C. As a result, the reaction was terminated at the time of 65 hours after starting reaction to give (1R)-1-(2-chlorophenyl)-2-nitroethanol quantitatively. The optical purity was 91% ee.

EXAMPLES 15 TO 22

Synthesis of various kinds of optically active β-nitroalcohls

The reaction was carried out in the same manner used in Example 1 except that the aldehyde compounds shown in Table 4 were used instead of 2-naphthadehyde, the amount of a catalyst was 5 mol % and the amount of diisopropylethylamine added was 2.5 times moles, based on the aldehydes, and the reaction temperature was the temperatures shown in Table 4. The reaction time, and the yield and the optical purity of the optically active β-nitroalcohol {$R^1$—C*H(OH)—$CH_2NO_2$} obtained were shown in Table 4.

TABLE 4

| Example | $R^1$ in the above-mentioned formula (a) | Reaction temperature/ ° C. | Reaction time/ h | Yield/ % | Optical purity/ % ee |
|---|---|---|---|---|---|
| 15 | p-ClPh | −78 | 72 | quantitative | 85 |
| 16 | o-FPh | −78 | 40 | 98 | 92 |
| 17 | o-CF$_3$Ph | −78 | 62 | 93 | 90 |
| 18 | o-BrPh | −78 | 70 | 85 | 84 |
| 19 | o-MeOPh | −40 | 90 | quantitative | 83 |
| 20 | Ph(CH$_2$)$_2$— | −78 | 41 | 83 | 81 |
| 21 | PhCH$_2$OCH$_2$— | −78 | 40 | 83 | 81 |
| 22 | Cyclohexyl | −78 | 112 | 91 | 73 |

EXAMPLE 23

The reaction was carried out in the same manner used in Example 1 except that cinnamaldehyde was used instead of 2-naphthaldehyde and the reaction temperature was −65° C. As a result, the reaction was terminated at the time of 90 hours after starting reaction to give the corresponding optically active β-nitroalcohol in yield of 72%. The optical purity was 79% ee.

EXAMPLES 24 TO 28

The reaction was carried out in the same manner used in Example 2 except that the optically active cobalt (II) complex catalyst or the optically active cobalt (III) complex catalyst having (S, S) absolute configuration shown in Table 5 was used instead of the optically active metal complex catalyst (c-4). The reaction temperature, the reaction time, and the yield and the optical purity of the resultant (1R)-1-(2-naphthyl)-2-nitroethanol in each Example were shown in Table 5.

TABLE 5

| Example | Optically active cobalt complex catalyst | Reaction temperature/ ° C. | Reaction time/ h | Yield/ % | Optical purity/ % ee |
|---|---|---|---|---|---|
| 24 | (c-1) | −60 | 67 | 64 | 19 |
| 25 | (c-3) | −60 | 67 | 82 | 55 |
| 26 | (c-5) | −60 | 67 | 93 | 12 |
| 27 | (c-11) | −50 | 21 | 82 | 63 |
| 28 | (c-13) | −40 | 21 | 58 | 69 |

EXAMPLES 29 TO 32

The reaction was carried out in the same manner used in Example 11 except that the optically active cobalt (II) complex catalyst having (S, S) absolute configuration shown in Table 6 was used as an optically active metal complex catalyst, and the reaction temperature was −65° C. The reaction time, and the yield and the optical purity of the resultant (1R)-1-(2-chlorophenyl)-2-nitroethanol were shown in Table 6.

TABLE 6

| Example | Optically active cobalt complex catalyst | Reaction time/ h | Yield/ % | Optical purity/ % ee |
|---|---|---|---|---|
| 29 | (c-3) | 64 | 92 | 70 |
| 30 | (c-4) | 24 | 88 | 84 |
| 31 | (c-5) | 64 | 97 | 49 |
| 32 | (c-6) | 64 | 99 | 40 |

EXAMPLES 33 AND 34

The reaction was carried out in the same manner used in Example 11 except that the optically active cobalt (III) complex catalyst having (S, S) absolute configuration shown in Table 7 was used instead of the optically active metal complex catalyst (c-4), the amount of diisopropylethylamine used as a base was 3 times moles based on aldehydes, and the reaction temperature was −70° C. The reaction time, and the yield and the optical purity of the resultant (1R)-1-(2-chlorophenyl)-2-nitroethanol in each Example were shown in Table 7.

TABLE 7

| Example | Optically active cobalt complex catalyst | Reaction time/ h | Yield/ % | Optical purity/ % ee |
|---|---|---|---|---|
| 33 | (c-13) | 42 | quantitative | 83 |
| 34 | (c-14) | 44 | quantitative | 72 |

EXAMPLE 35

The reaction was carried out in the same manner used in Example 11 except that the optically active cobalt (II) complex catalyst (c-7) (2 mol %) having (S, S) absolute configuration was used instead of the optically active metal complex catalyst (c-4), and the reaction temperature was −78° C. The reaction was terminated at the time of 95 hours after starting the reaction to give (1R)-1-(2-chlorophenyl)-2-nitroethanol quantitatively. The optical purity was 95% ee.

EXAMPLES 36 AND 37

The reaction was carried out in the same manner used in Example 35 except that the aldehyde compounds shown in Table 8 were used instead of 2-chlorobenzaldehyde. The reaction time, and the yield and the optical purity of the optically active β-nitroalcohol obtained were shown in Table 8

TABLE 8

| Example | $R^1$ in the above-mentioned formula (a) | Reaction time/ h | Yield/ % | Optical purity/ % ee |
|---|---|---|---|---|
| 36 | o-FPh | 18 | quantitative | 98 |
| 37 | o-BrPh | 94 | quantitative | 94 |

EXAMPLE 38

The reaction was carried out in the same manner used in Example 1 except that the optically active cobalt (II) complex catalyst (c-8) (2 mol %) having (S, S) absolute configuration was used instead of the optically active metal complex catalyst (c-4), and the reaction temperature was −78° C. The reaction was terminated at the time of 47 hours after starting the reaction to give (1R)-1-(2-naphthyl)-2-nitroethanol in yield of 12%. The optical purity was 51% ee.

EXAMPLES 39 AND 40

The reaction was carried out in the same manner used in Example 38 except that the aldehydes compounds shown in Table 9 were used instead of 2-naphthaldehyde. The reaction time, and the yield and the optical purity of the optically active β-nitroalcohol obtained were shown in Table 9.

TABLE 9

| Example | $R^1$ in the above-mentioned formula (a) | Reaction time/ h | Yield/ % | Optical purity/ % ee |
|---|---|---|---|---|
| 39 | p-ClPh | 98 | 45 | 88 |
| 40 | Ph(CH$_2$)$_2$— | 45 | 64 | 93 |

INDUSTRIAL APPLICABILITY

According to the production method of present invention, it is possible to produce asymmetric nitroalcohols using a smaller amount of catalyst for a shorter time, compared with the production method using a conventional asymmetric catalyst. The optically active nitroalcohols are useful as optically active intermediates of physiologically active compounds such as medicines and agricultural chemicals, and are useful as starting materials for synthesis of functional materials or fine chemicals.

What is claimed is:

1. A process for producing optically active β-nitroalcohols, wherein nitroaldol reactions of aldehydes and nitroalkanes are carried out in the presence of a base and an optically active metal complex catalyst represented by the following formula (c):

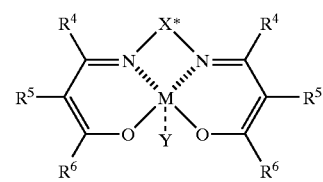

(where $R^4$, $R^5$, and $R^6$ represent independently a hydrogen atom, a straight, branched or cyclic alkyl group, a straight or branched alkenyl group, an aryl group, an acyl group, an alkoxycarbonyl group, an aryloxycarbonyl group, or an aralkyloxycarbonyl group, each of which may have a substituent, and $R^5$ and $R^6$ may be linked together to form a ring; X* represents a hydrocarbon group of 4 or more carbon atoms having an asymmetric carbon atom or axial asymmetry; M represents a cobalt ion or a chromium ion; and Y represents an anion capable of forming a salt when the valence of M is larger than that of a ligand, and Y does not exist when the valences of a metal ion and a ligand are equal to each other).

2. The process for producing optically active β-nitroalcohols according to claim 1, wherein the aldehydes are represented by the following general formula (a):

$$R^1CHO \qquad (a)$$

(where $R^1$ represents a straight, branched or cyclic alkyl group, a straight, branched or cyclic alkenyl group, a straight or branched alkynyl group, an aryl group, an aralkyl group, an aralkenyl group, or an aralkynyl group, each of which may have a substituent).

3. The process for producing optically active β-nitroalcohols according to claim 1, wherein the nitroalkanes are represented by the following general formula (b):

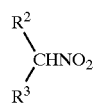

(where $R^2$ and $R^3$ represent independently a hydrogen atom or an optionally substituted alkyl group, and $R^2$ and $R^3$ may be linked together to form a ring).

4. The process for producing optically active β-nitroalcohols according to claim 2, wherein the nitroalkanes are represented by the following general formula (b):

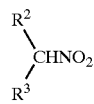

(where $R^2$ and $R^3$ represent independently a hydrogen atom or an optionally substituted alkyl group, and $R^2$ and $R^3$ may be linked together to form a ring).

5. The process for producing optically active β-nitroalcohols according to claim 1, wherein the hydrocarbon group X* in the general formula (c) is a hydrocarbon group represented by any one of the following general formulas (x-1), (x-2), and (x-3):

23

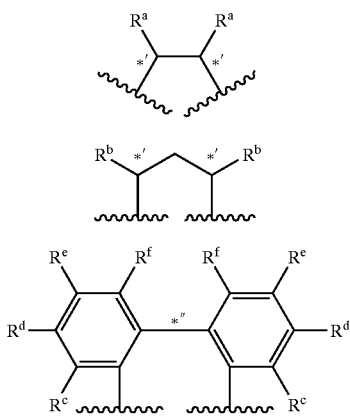

(x-1)

(x-2)

(x-3)

(where $R^a$ and $R^b$ represent a straight, branched or cyclic alkyl group, or an aryl group, each of which may have a substituent, and two $R^a$ groups may be linked together to form a ring; $R^c$, $R^d$, $R^e$, and $R^f$ represent independently a hydrogen atom, a halogen atom, a straight, branched or cyclic alkyl group, an aryl group, or an alkoxy group, each of which may have a substituent, $R^e$ and $R^f$ may be linked together to form a ring, and the ring may have a substituent; *' represents an asymmetric carbon atom; and *" represents axial asymmetry).

6. The process for producing optically active β-nitroalcohols according to claim 2, wherein the hydrocarbon group X* in the general formula (c) is a hydrocarbon group represented by any one of the following general formulas (x-1), (x-2), and (x-3):

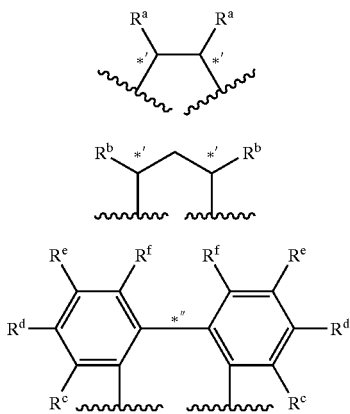

(x-1)

(x-2)

(x-3)

(where $R^a$ and $R^b$ represent a straight, branched or cyclic alkyl group, or an aryl group, each of which may have a substituent, and two $R^a$ groups may be linked together to form a ring; $R^c$, $R^d$, $R^e$, and $R^f$ represent independently a hydrogen atom, a halogen atom, a straight, branched or cyclic alkyl group, an aryl group, or an alkoxy group, each of which may have a substituent, $R^e$ and $R^f$ may be linked together to form a ring, and the ring may have a substituent: *' represents an asymmetric carbon atom; and *" represents axial asymmetry).

7. The process for producing optically active β-nitroalcohols according to claim 3, wherein the hydrocarbon group

24

X* in the general formula (c) is a hydrocarbon group represented by any one of the following general formulas (x-1), (x-2), and (x-3)

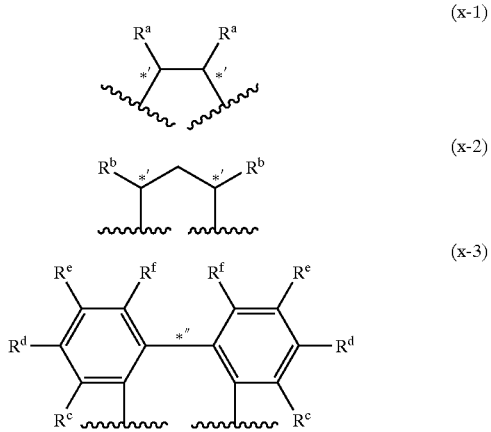

(x-1)

(x-2)

(x-3)

(where $R^a$ and $R^b$ represent a straight, branched or cyclic alkyl group, or an aryl group, each of which may have a substituent, and two $R^a$ groups may be linked together to form a ring, $R^c$, $R^d$, $R^e$, and $R^f$ represent independently a hydrogen atom, a halogen atom, a straight, branched or cyclic alkyl group, an aryl group, or an alkoxy group, each of which may have a substituent, $R^e$ and $R^f$ may be linked together to form a ring, and the ring may have a substituent; *' represents an asymmetric carbon atom; and *" represents axial asymmetry).

8. The process for producing optically active β-nitroalcohols according to claim 4, wherein the hydrocarbon group X* in the general formula (c) is a hydrocarbon group represented by any one of the following general formulas (x-1), (x-2), and (x-3):

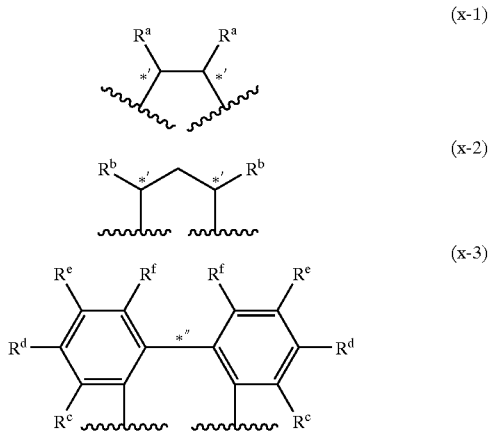

(x-1)

(x-2)

(x-3)

(where $R^a$ and $R^b$ represent a straight, branched or cyclic alkyl group, or an aryl group, each of which may have a substituent, and two $R^a$ groups may be linked together to form a ring; $R^c$, $R^d$, $R^e$, and $R^f$ represent independently a hydrogen atom, a halogen atom, a straight, branched or cyclic alkyl group, an aryl group, or an alkoxy group, each of which may have a substituent, $R^e$ and $R^f$ may be linked together to form a ring, and the ring may have a substituent; *' represents an asymmetric carbon atom; and *" represents axial asymmetry).

9. The process for producing optically active β-nitroalcohols according to claim 8, wherein the base is a compound selected from the group consisting of primary amines, secondary amines, and tertiary amines.

10. The process for producing optically active β-nitroalcohols according to claim 1, wherein the base is a compound selected from the group consisting of primary amines, secondary amines, and tertiary amines.

11. The process for producing optically active β-nitroalcohols according to claim 2, wherein the base is a compound selected from the group consisting of primary amines, secondary amines, and tertiary amines.

12. The process for producing optically active β-nitroalcohols according to claim 3, wherein the base is a compound selected from the group consisting of primary amines, secondary amines, and tertiary amines.

13. The process for producing optically active β-nitroalcohols according to claim 4, wherein the base is a compound selected from the group consisting of primary amines, secondary amines, and tertiary amines.

14. The process for producing optically active β-nitroalcohols according to claim 5, wherein the base is a compound selected from the group consisting of primary amines, secondary amines, and tertiary amines.

15. The process for producing optically active β-nitroalcohols according to claim 6, wherein the base is a compound selected from the group consisting of primary amines, secondary amines, and tertiary amines.

16. The process for producing optically active β-nitroalcohols according to claim 7, wherein the base is a compound selected from the group consisting of primary amines, secondary amines, and tertiary amines.

* * * * *